United States Patent [19]
McFall et al.

[11] Patent Number: 5,756,039
[45] Date of Patent: May 26, 1998

[54] METHOD AND APPARATUS FOR FORMING A MULTI-SEGMENT CORE

[75] Inventors: Ronald Ray McFall; David Christopher Oetjen, both of West Chester, Ohio

[73] Assignee: The Procter & Gamble Company, Cincinnati, Ohio

[21] Appl. No.: 627,617

[22] Filed: Apr. 4, 1996

Related U.S. Application Data

[63] Continuation of Ser. No. 225,191, Apr. 8, 1994, Pat. No. 5,591,148.

[51] Int. Cl.$^6$ .................. A61F 13/15; B27N 3/04
[52] U.S. Cl. .................. 264/517; 264/118; 264/121; 425/80.1; 425/81.1
[58] Field of Search .................. 264/517, 118, 264/121; 425/80.1, 81.1

[56] References Cited

U.S. PATENT DOCUMENTS

| | | | |
|---|---|---|---|
| 3,071,138 | 1/1963 | Garcia | 128/290 |
| 3,939,240 | 2/1976 | Savich | 264/517 |
| 3,954,107 | 5/1976 | Chesky | 128/290 R |
| 4,340,058 | 7/1982 | Pierce | 128/290 B |
| 4,388,056 | 6/1983 | Lee et al. | 425/83.1 |
| 4,589,876 | 5/1986 | Van Tilburg | 604/385 R |
| 4,592,708 | 6/1986 | Feist et al. | 425/80.1 |
| 4,666,647 | 5/1987 | Enloe et al. | 264/121 |
| 4,859,388 | 8/1989 | Peterson et al. | 264/121 |
| 4,908,175 | 3/1990 | Angstadt | 264/113 |
| 4,915,897 | 4/1990 | Farrington et al. | 264/517 |
| 4,973,325 | 11/1990 | Sherrod et al. | 604/368 |
| 5,004,579 | 4/1991 | Wislinski et al. | 264/517 |
| 5,248,309 | 9/1993 | Serbiak et al. | 604/368 |
| 5,304,161 | 4/1994 | Noel et al. | 604/378 |
| 5,342,337 | 8/1994 | Runeman et al. | 604/378 |

FOREIGN PATENT DOCUMENTS

| | | |
|---|---|---|
| 0687453A1 | 6/1995 | European Pat. Off. |
| 3508344A1 | 9/1986 | Germany. |
| 8499 | of 1914 | United Kingdom. |
| WO 94/05243 | 3/1994 | WIPO. |

*Primary Examiner*—Mary Lynn Theisen
*Attorney, Agent, or Firm*—Gerry S. Gressel; Larry L. Huston; E. Kelly Linman

[57] ABSTRACT

An apparatus and method are disclosed for forming a sanitary napkin having a multi-segment core. Such a core is formed using a mold having a deposition cavity which is divided into cavity segments by at least one partition. Each partition can comprise a passageway for interconnecting adjacent cavity segments.

5 Claims, 8 Drawing Sheets

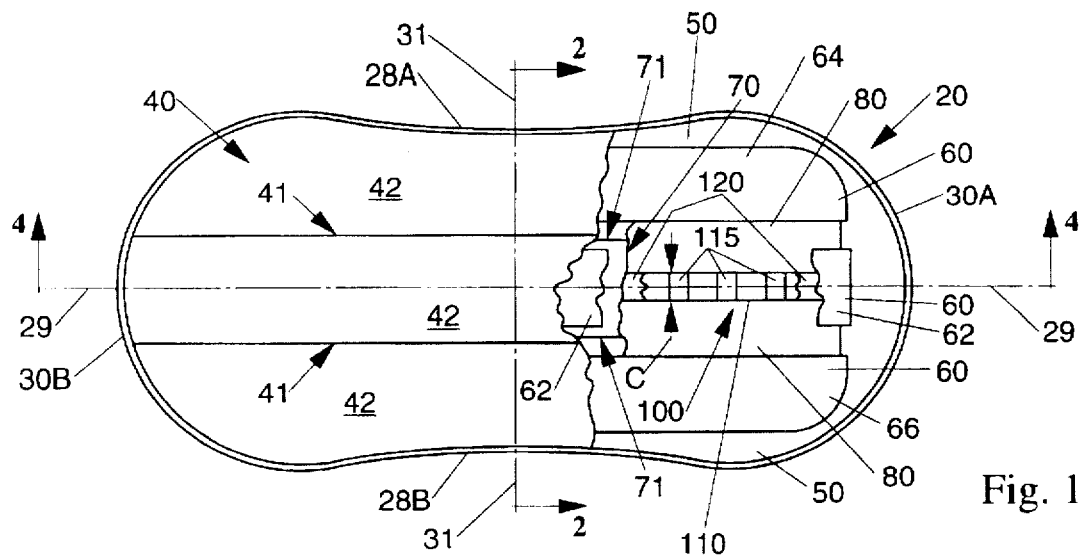
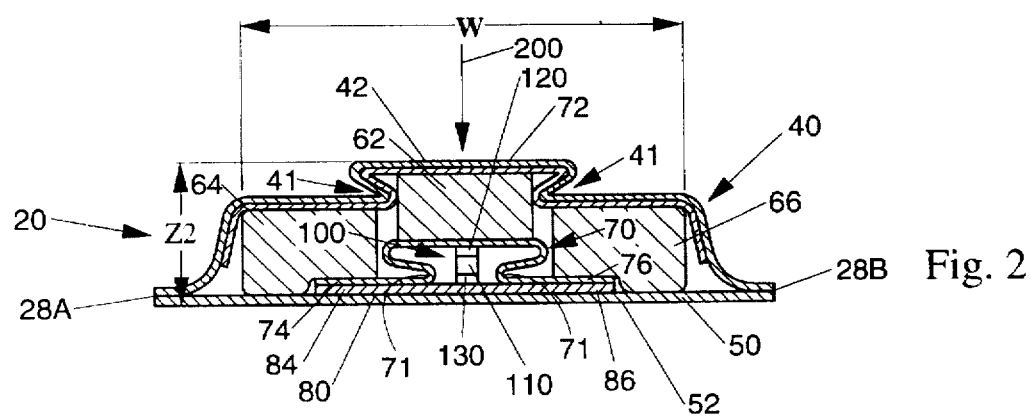

METHOD AND APPARATUS FOR FORMING A MULTI-SEGMENT CORE

This application claims priority to, and is a continuation of application Ser. No. 08/225,191, filed on Apr. 8, 1994, now U.S. Pat. No. 5,591,148.

FIELD OF THE INVENTION

The present invention relates generally to disposable absorbent articles such as sanitary napkins and, more particularly, to a sanitary napkin having an absorbent core comprising distinct core segments, and a lifting member for providing independent displacement of at least one of the core segments relative to the other core segments

BACKGROUND OF THE INVENTION

Absorbent articles such as sanitary napkins, pantiliners, and incontinence pads are designed to absorb and retain liquid and other discharges from the human body, and to prevent soiling of the body and clothing by such discharges. It is generally desirable to provide absorbent articles such as sanitary napkins which maintain contact with the body of the wearer when they are worn, and which conform as closely as possible to the body of the wearer. Such body conforming capability is believed to increase the effectiveness of the sanitary napkin by reducing the possibility that menses will travel around the perimeter of the sanitary napkin and soil the wearer's body and/or clothing.

There have been a number of recent efforts to provide sanitary napkins and other absorbent articles with improved fit characteristics. Such recent efforts are described in U.S. Pat. No. 4,950,264 issued Aug. 21, 1990 to Osborn, U.S. Pat. No. 5,007,906 issued Apr. 16, 1991 to Osborn; U.S. Pat. No. 5,197,959 issued Mar. 30, 1993 to Buell; U.S. patent application Ser. No. 07/605,583, now abandoned, entitled "Sanitary Napkin Having Components Capable of Separation In Use" filed Oct. 29, 1990 in the name of Visscher et al.; and PCT International Publication Number WO 92/07535 published May 14, 1992 in the name of Visscher et al. In addition, the following commonly assigned and copending U.S. Patent Applications provide sanitary napkins having internal shaping components and lifting members: "Sanitary Napkin Having a Pleated Lifting Member," Ser. No. 08/170,461, now abandoned, filed Dec. 20, 1993 in the name of McFall; and "Sanitary Napkin Having an Internal Shaping Component," Ser. No. 08/170,487, now abandoned, filed Dec. 20, 1993 in the name of Bergman.

There have also been efforts to provide a disposable absorbent articles having two or more absorbent portions or layers. The following documents describe disposable absorbent articles having multiple absorbent portions or layers: Great Britain Patent 23,103 issued Oct. 28, 1915 to Mycroft; U.S. Pat. No. 3,071,138 issued Jan. 1, 1963 to Garcia; U.S. Pat. No. 3,653,382 issued Apr. 4, 1972 to Easley et al.; U.S. Pat. No. 3,954,107 issued May 4, 1976 to Chesky et al.; U.S. Pat. No. 4,340,058 issued Jul. 20, 1982 to Pierce; U.S. Pat. No. 4,589,876 issued May 20, 1986 to Van Tilburg; U.S. Pat. No. 4,973,325 issued Nov. 27, 1990 to Sherrod et al; U.S. Pat. No. 4,988,344 issued Jan. 29, 1991 to Reising et al.; and U.S. patent application Ser. No. 07/827,555 entitled "Sanitary Napkin Having Transversely Segmented Core," filed in the name of Osborn, Ill. on Jan. 28, 1992, now abandoned (continuation of Ser. No. 07/630,451 filed Dec. 19, 1990, now abandoned).

While the sanitary napkins disclosed in these references represent advancements in the art, the search for new and different ways of improving body contact has continued.

It is especially desirable that the sanitary napkin maintain contact with and conform to the body of the wearer under dynamic conditions (when the wearer walks, sits, etc.). For instance, when the sanitary napkin is worn, the sanitary napkin is subjected to lateral compression by the upper portions of the wearer's thighs. The forces applied by the wearer's thighs generally tend to distort the shape of the sanitary napkin, reducing the size of the target the sanitary napkin provides.

One attempt to control the effect of these compressive forces is disclosed in UK Patent Application 2,168,612A, published Jun. 25, 1986. The UK patent application discloses a sanitary towel with a resilient insert positioned within the core or adjacent to a face of the core that is intended to inhibit permanent distortion of the towel. The UK application teaches that the insert resists lateral deformation of the sanitary towel, but does not teach or disclose a sanitary napkin having body conforming properties.

It is also desirable to provide a sanitary napkin which conforms to the wearer's body while maintaining the comfort of the wearer. Accordingly, a desirable sanitary napkin should maintain contact with the wearer's body, yet be capable of repeated elastic deflection to allow the wearer to comfortably assume different positions and to perform different activities.

It is therefore an object of this invention to provide an absorbent article, such as a sanitary napkin, which intercepts menses by conforming to the shape of the female urogenital region.

It is another object of the present invention to provide an absorbent article having a bi-level core and a bi-level body facing surface.

Another object of the present invention to provide a sanitary napkin having separate core segments.

Yet another object of the present invention is to provide a sanitary napkin having a lifting member for displacing a central absorbent core segment relative to side absorbent core segments.

These and other objects of the present invention will be more readily apparent when considered in reference to the following description and when taken in conjunction with the accompanying drawings.

SUMMARY OF THE INVENTION

The present invention provides an apparatus for forming an airlaid absorbent core having multiple segments. The apparatus comprises a mold, which can be disposed on the circumference of an airfelt laydown drum. The mold has a top surface, a deposition cavity formed in the top surface, and at least one partition dividing the deposition cavity into cavity segments. The deposition cavity is bounded by a perimeter side wall and a foraminous bottom wall.

In one embodiment, the mold has a pair of generally parallel partitions which extend circumferentially to be generally parallel to the direction of rotation of the laydown drum.

Each partition can comprise a passageway, such as slots, for interconnecting adjacent cavity segments.

BRIEF DESCRIPTION OF THE DRAWINGS

FIG. 1 is a top plan view of a sanitary napkin of the present invention with portions of the sanitary napkin shown cut away to reveal separate core segments.

FIG. 2 is a section view taken along line 2—2 of FIG. 1 which shows the sanitary napkin of the present invention in a compressed configuration.

DETAILED DESCRIPTION OF THE INVENTION

FIGS. 1–4 illustrate a sanitary napkin 20 according to one embodiment of the disposable absorbent article of the present invention. As used herein, the term "absorbent article" refers to articles which absorb and contain body exudates. More specifically, the term is intended to include, but not be limited to, sanitary napkins, pantiliners, and incontinence pads (articles worn in the crotch region of a garment). The term "disposable" refers to articles which are intended to be discarded after a single use rather than laundered or otherwise restored or reused.

The sanitary napkin 20 has a perimeter having first and second longitudinally extending sides 28A and 28B joining first and second laterally extending ends 30A and 30B. The sanitary napkin also has a longitudinal centerline 29 and a lateral centerline 31. As used herein the term "longitudinal" refers to a line, axis, or direction generally aligned with the vertical plane which bisects the standing wearer into left and right body halves. The term "lateral" refers to a line, axis, or direction generally perpendicular to the longitudinal direction and lying within the plane of the sanitary napkin 20. The sanitary napkin 20 is typically longer in the longitudinal direction than in the lateral direction.

Figure 3:
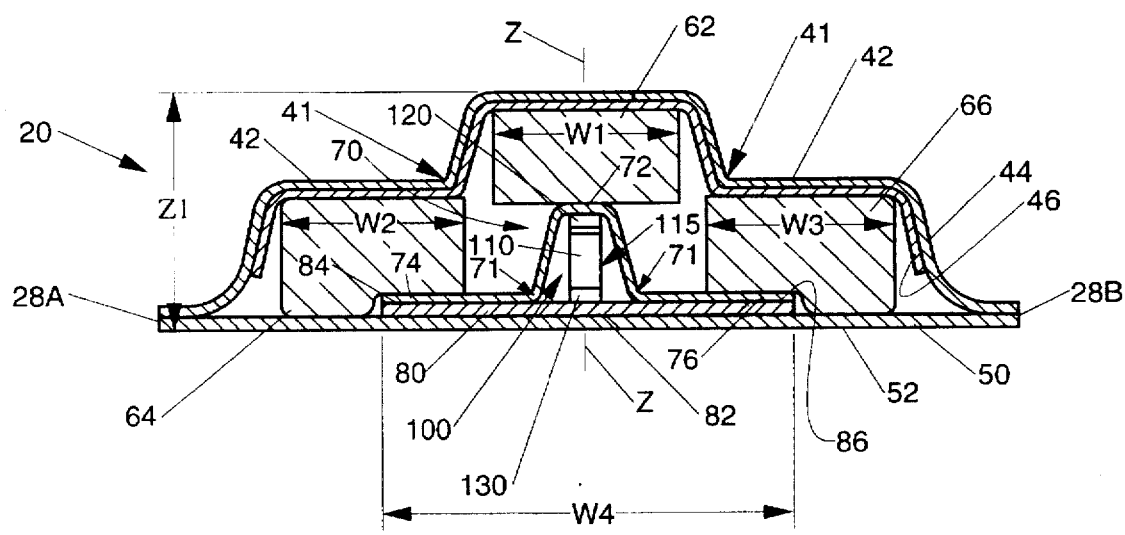
FIG. 3 is a section view of the sanitary napkin of FIG. 2 shown in an extended configuration.

The "Z" direction refers to a line, axis, or direction which is perpendicular to the plane of the sanitary napkin (i.e., perpendicular to both the longitudinal axis 29 and the lateral axis 31 when the sanitary napkin is supported in a generally flat configuration). The Z direction is illustrated in FIG. 3.

The sanitary napkin 20 according to the present invention comprises a liquid pervious topsheet 40 having a body facing surface 42; a liquid impervious backsheet 50 having a garment facing surface 52; and an absorbent core 60 disposed intermediate the topsheet 40 and the backsheet 50.

The absorbent core 60 comprises a three piece construction which includes a central core segment 62 extending along the longitudinal centerline 29, a first longitudinally extending side core segment 64, and a second longitudinally extending side core segment 66. The first and second core side segments 64 and 66 are disposed intermediate the longitudinal centerline 29 and the first and second longitudinally extending sides 28A and 28B of the sanitary napkin 20, respectively. The absorbent core 60 has a longitudinal length L (FIG. 4) measured along the longitudinal centerline 29 which is typically greater than the absorbent core's lateral width W (FIG. 2) measured along the lateral centerline 31.

The sanitary napkin 20 according to the present invention further comprises a lifting member 100 disposed intermediate the backsheet 50 and the central core segment 62. The lifting member 100 can be disposed laterally intermediate the first and second core side segments 64 and 66. The lifting member 100 provides Z-direction elastic displacement of the central core segment 62 relative to the first and second side core segments 64 and 66 and the backsheet 50.

Figure 4:
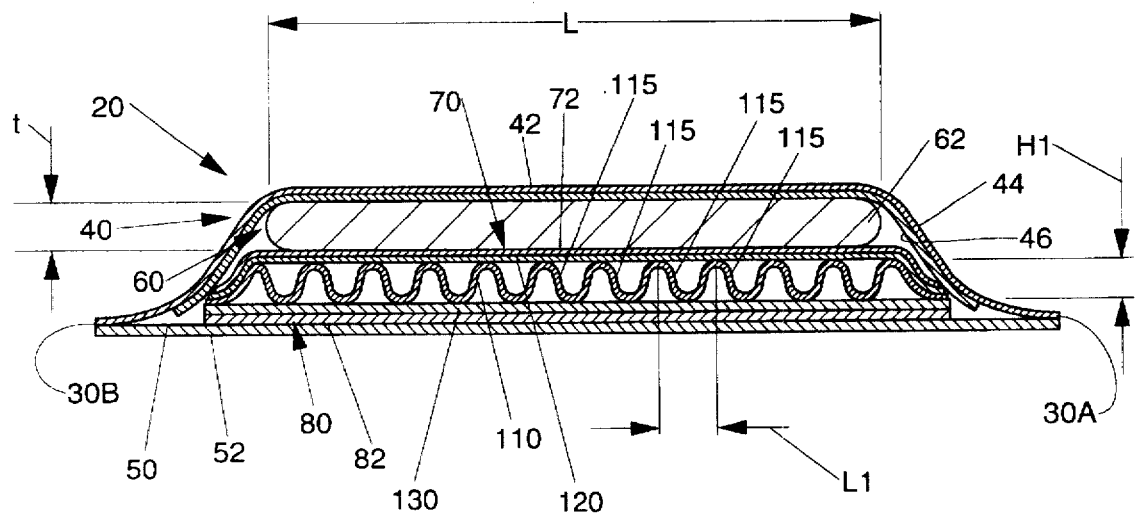
FIG. 4 is a section view taken along line 4—4 of FIG. 1 which shows a sanitary napkin of the present invention in an extended configuration, and a lifting member with pleats of generally uniform Z-direction height, the pleats extending along the longitudinal centerline of the sanitary napkin.

By "Z-direction elastic displacement" of the central core segment 62 relative to the backsheet 50 and the side core segments 64,66, it is meant that the central core segment 62 can be displaced relative to the backsheet 50 and the side core segments 64,66 in the Z-direction from a first, extended configuration, wherein the sanitary napkin 20 has a Z-direction caliper Z1 shown in FIGS. 3 and 4, to a second compressed configuration having a caliper Z2 shown in FIG. 2 (such as by the compressive Z-direction load 200), and that the lifting member 100 will restore the sanitary napkin 20 to have a Z-direction caliper which is at least about 70 percent of the Z-direction caliper Z1 upon release of the compressive loading, when the sanitary napkin is dry and has not been loaded with body exudates. The elastic displacement of the topsheet 22 relative to the backsheet 24 can be expressed by the difference Z1–Z2.

The Z-direction calipers Z1 and Z2, and the corresponding Z-direction compressive loading are measured using a suitable tensile testing machine, such as an Instron Model 4502 tensile testing machine manufactured by the Instron Engineering Corporation of Canton, Mass. The Z-direction calipers Z1 and Z2 are measured using the procedure described in U.S. patent application Ser. No. 08/170,461, Sanitary Napkin Having a Pleated Lifting Member, filed Dec. 20, 1993 in the name of McFall, which application is incorporated herein by reference.

By lifting the central core segment 62 relative to the side core segments 64, 66, the lifting member 100 maintains contact of a portion of the topsheet 40 overlying the central core segment 62 and extending along the longitudinal centerline 29 with the wearer's body. The lifting member 100 convexly shapes the body facing surface 42 of the topsheet 40 to conform to the wearer's body, particularly in the labia, perineum, and/or gluteal groove areas. The lifting member 100 also biases the central core segment 62 into engagement with the portion of the topsheet 40 along the longitudinal centerline 29 to enhance acquisition of body fluids by the central core segment 62 from the portion of the topsheet 40 extending along the longitudinal centerline 29.

The central core segment 62 preferably has a lateral width W1 (FIG. 3) measured along the lateral centerline 31 which is less than the lateral width W of the absorbent core 60. A lateral width W1 which is less than the lateral width W reduces the weight of absorbent material displaced by the lifting member 100. Reducing the weight of absorbent material displaced by the lifting member 100 reduces the required stiffness of the lifting member 100, and thereby provides a more comfortable fit for the wearer. The side core segments 64 and 66 preferably have lateral widths W2 and W3 which are less than the width W of the absorbent core 60. The side core segments 64 and 66 can be laterally spaced apart a distance greater than the width W1 so that the center core segment 62 is positioned laterally intermediate the side core segments 64 and 66 when the sanitary napkin 20 is compressed as shown in FIG. 2.

The lifting member 100 displaces the central core segment 62 to extend above the plane of the side core segments 64 and 66. The lifting member 100 thereby provides a bi-level core 60 and a bi-level body facing surface 42 of the topsheet. Such a bi-level core 60 and bi-level body facing surface 42 improves body fit by providing enhanced contact with the labia, perineum, and gluteal groove areas of the body. In addition, a lateral width W1 which is less than the lateral width W promotes convex shaping of the body facing surface 42 of the topsheet 40 along the longitudinal centerline 29, and thereby enhances fit in the labia, perineum, and/or gluteal groove areas of the body.

The central core segment 62 is preferably separate from the first and second core side segments 64 and 66. The central core segment should be separate from the first and second core segments 64 and 66 so that the lifting member 100 can displace the central core segment 62 independently of the side core segments 64 and 66. By the term "separate" it is meant that the central core segment 62 is not an extension of, nor directly joined or directly connected to either of the first and second core side segments 64 and 66 by adhesive or other fastening means. Of course, the central core segment 62 can be separate from the first and second side core segments 64 and 66 and yet be indirectly joined to the side core segments 64 and 66 by one or more other elements of the sanitary napkin 20. For instance, the topsheet 40 can be directly joined to each of the core segments 62, 64, and 66, and thereby indirectly join the core segments 62, 64 and 66.

Referring to FIGS. 2 and 3, the sanitary napkin 20 according to the present invention can have a wicking member 70 for conveying body fluids from the central core segment 62 to the first and second side core segments 64 and 66. The wicking member 70 can also provide lateral support for the lifting member 100 when the sanitary napkin 20 is in the extended position shown in FIGS. 3 and 4. The wicking member 70 can comprise a web of cellulosic fibers, such as a web of tissue paper. The wicking member 70 can have a first longitudinally extending side portion 74, a second longitudinally extending side portion 76, and a longitudinally extending central portion 72 extending laterally intermediate the first and second side portions 74 and 76. The first side portion 74 is disposed intermediate the first side core segment portion 64 and the backsheet 50. The second side portion 76 is disposed intermediate the second side core segment 66 and the backsheet 50. The central portion 72 is disposed intermediate the central core segment 62 and the lifting member 100. The wicking member 70 can have a pair of longitudinally extending folds 71 for accommodating extension of the lifting member 100 in the Z-direction.

The sanitary napkin 20 according to the present invention can also have a support member 80. The support member 80 has a lateral width greater than the lateral width of the lifting member 100 and distributes loads from the lifting member 100 to the backsheet 50. The support member 80 also stiffens the structure of the sanitary napkin 20 underlying the lifting member 100. The support member 80 thereby helps to ensure that the lifting member 100 displaces the central core segment 62 upward relative to the side core segments 64 and 66 and the backsheet 50.

The support member 80 can extend laterally intermediate the first and second side core segments 64 and 66, and can comprise a web of cellulosic fibers, such as a web of tissue paper. The support member 80 can have a first longitudinally extending side portion 84, a second longitudinally extending side portion 86, and a longitudinally extending central portion 82 extending laterally intermediate the first and second side portions 84 and 86. The central portion 82 is joined to the lifting member 100 and at least the first and second side portions are joined to the backsheet 50. The first side portion 84 is disposed intermediate the first side core segment 64 and the backsheet 50. The second side portion 86 is disposed intermediate the second side core segment 66 and the backsheet 50. The central portion 82 is disposed intermediate the lifting member 100 and the backsheet 50. The wicking member 70 and the support member 80 preferably have a lateral width less than the width W of the absorbent core 60 to prevent wicking of body exudates to the longitudinally extending sides 28A and 28B of the sanitary napkin 20. In the embodiment shown in FIGS. 1 through 4 the central portion 72 of the wicking member 70 is joined to the lifting member 100, and the side portions 74 and 76 of the wicking member are joined to the side portions 84 and 86, respectively, of the support member 80.

Examining the components of the sanitary napkin 20 in more detail, the topsheet 40 is the component of the sanitary napkin 20 oriented towards and contacting the body of the wearer for receiving body exudates. The topsheet 40 is flexible, soft feeling, non-irritating to the wearer's skin, and is liquid pervious. As used herein, the term flexible refers to materials which are compliant and readily conform to the shape of the body or respond by easily deforming in the presence of external forces. Preferably, the topsheet 40 is not noisy to provide discretion to the wearer.

The topsheet 40 should be clean in appearance and can be somewhat opaque to hide the discharges collected in the core 60. The topsheet 40 preferably has a pair of laterally spaced apart and longitudinally extending folds 41. The folds 41 in the topsheet 40 accommodate the Z-direction displacement of the central core segment 62. The folds 41 also permit independent Z-direction displacement of the central core segment 62 relative to the core segments 64 and 66 when all three core segments are joined to the topsheet 40.

The topsheet 40 is preferably joined to the backsheet along the longitudinal sides 28A and 28B and along one or both of the lateral ends 30A and 30B. The topsheet 40 can be joined to the backsheet 50 to provide Z-direction decoupling of the topsheet 40 from the backsheet 50, as described in U.S. Pat. No. 5,007,906 issued Apr. 16, 1991 to Osborn et al. which patent is incorporated herein by reference. The topsheet 40 can be joined to the backsheet 50 by any suitable method, including but not limited to adhesive bonding, ultrasonic bonding, or thermal bonding.

The topsheet 40 should exhibit good strike-through and rewet characteristics, permitting bodily discharges to rapidly penetrate the topsheet 40 and the core 60. A suitable topsheet 40 may be made from a wide range of materials, such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or combinations of natural and synthetic fibers.

Figure 5:
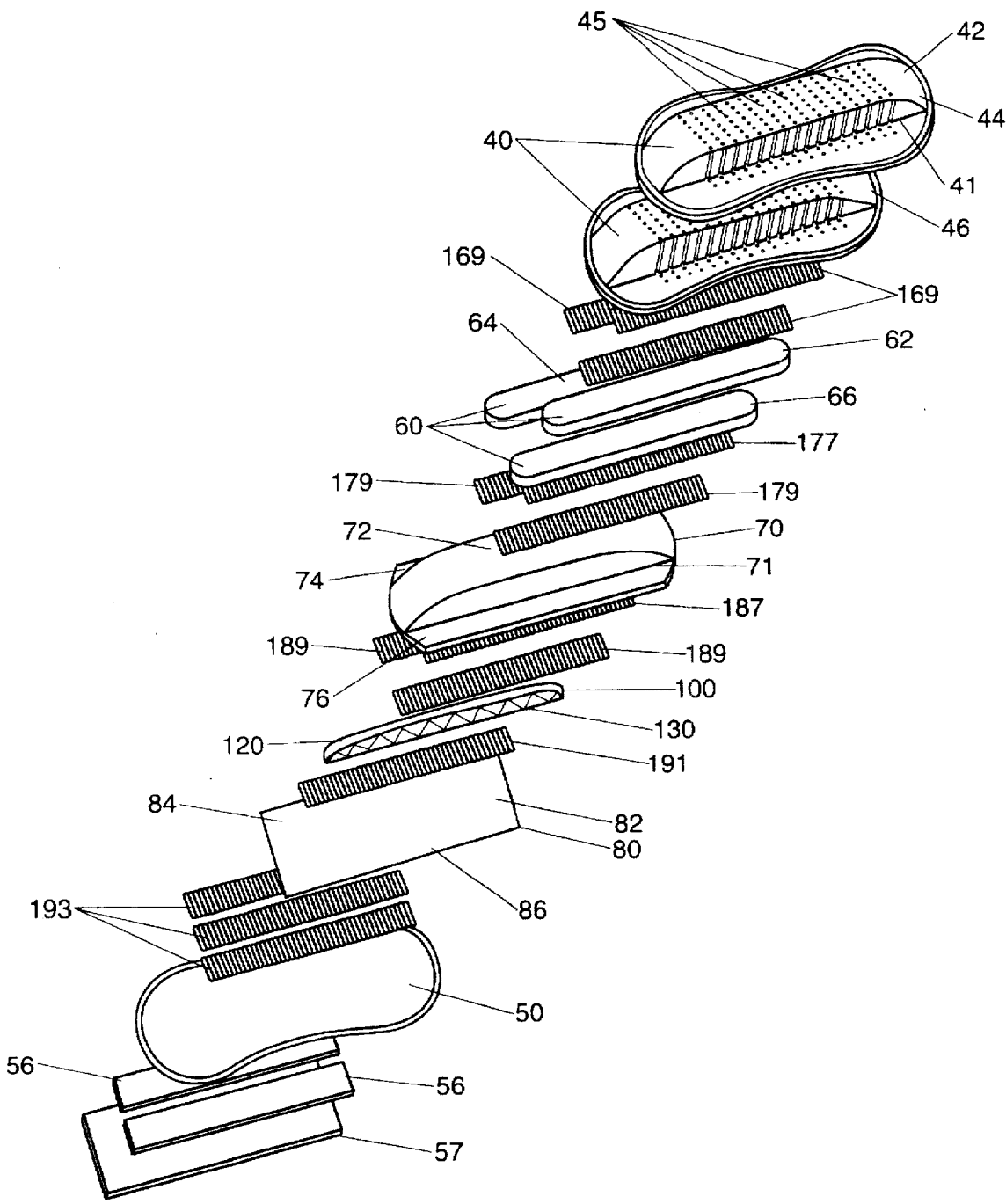
FIG. 5 is an exploded view of a sanitary napkin according to one embodiment of the present invention.

The topsheet 40 has a plurality of apertures to permit liquids deposited thereon to pass through to the core 60. The topsheet 40 can comprise an apertured formed polyolefinic film having about 5 to about 60 percent open area and a thickness of about 0.01 to about 0.05 millimeters. Referring to FIG. 5, the topsheet 40 can comprise a primary topsheet layer 44 joined to a secondary topsheet layer 46. The primary topsheet layer 44 can comprise an apertured formed polyolefinic film made in accordance with one of the following U.S. Patents: U.S. Pat. No. 3,929,135 issued Dec. 30, 1975 to Thompson; U.S. Pat. No. 4,324,246 issued Apr. 13, 1982 to Mullane; U.S. Pat. No. 4,342,314 issued Aug. 3, 1982 to Radel et al.; U.S. Pat. No. 4,463,045 issued Jul. 31, 1984 to Ahr et al.; and U.S. Pat. No. 5,006,394 issued Apr. 9, 1991 to Baird, which patents are incorporated herein by reference for the purpose of disclosing particularly preferred executions of liquid pervious topsheets.

The secondary topsheet layer 46 can comprise a nonwoven web of natural or synthetic fibers. Suitable nonwovens from which the secondary topsheet layer 46 can be formed include a nonwoven web of spunbond polypropylene fibers designated P-9 having a basis weight of about 18 grams per square yard and available from the Fiberweb Corporation of Simpsonville, S.C. under the tradename CELESTRA. Another suitable nonwoven from which the secondary topsheet layer 46 can be formed is an airthrough bonded fabric having a basis weight of about 21 grams per square meter formed of bicomponent fibers, the fibers having a polyethylene sheath and a polypropylene or polyester core. Such an airthrough bonded fabric is available from the Havix Company (formerly Fukumura) of Ijra-Mura Japan as S2416 airthrough bonded fabric.

The primary and secondary topsheet layers 44 and 46 are preferably joined together by a plurality of discrete bonds 45 (FIG. 5). The bonds 45 are preferably formed using the mechanical bonding method disclosed in U.S. Pat. No. 4,919,738 issued Apr. 24, 1990 to Ball et al., which patent is incorporate herein by reference. Alternatively, the layers 44 and 46 can be joined using other methods, including but not limited to adhesive bonding, ultrasonic bonding, and thermal bonding.

The backsheet 50 may be any flexible liquid impervious material, such as a polyolefinic film. The backsheet 50 prevents discharges collected by the sanitary napkin 20 from soiling the wearer or the wearer's clothing. The backsheet 50 can be a low density polyethylene film about 0.01 to about 0.05 millimeters in thickness, and preferably about 0.025 millimeters (1.0 mil). Suitable polyethylene films from which the backsheet 24 can be formed are sold by the Ethyl Corp., Visqueen Division, as Model XP-39385 and by the Clopay Corp. of Cincinnati, Ohio as SOFLEXX 1401.

The backsheet 50 can have a surface area greater than or equal to that of the topsheet 40 and the absorbent core 60, and preferably peripherally circumscribes the topsheet 40 and the core 60. The backsheet 40 may comprise flaps (not shown) extending outwardly from each longitudinally side 28A and 28B. The flaps may be made in accordance with the teachings of U.S. Pat. Nos. 4,589,876 issued May 20, 1986 to Van Tilburg and 4,687,478 issued Aug. 18, 1987 to Van Tilburg, which patents are incorporated by reference. The backsheet 50 and the flaps may be unitary and coextensive. Alternatively, the flaps can be separate components joined to the backsheet.

The garment facing surface 52 of the backsheet 50 may comprise an attachment means 56 (FIG. 5) for securing the sanitary napkin 20 to the undergarment of the wearer. Preferred attachment means 56 include mechanical fasteners, or more preferably, pressure sensitive adhesive. The pressure sensitive adhesive may be applied to the garment facing surface 52 in one or more strips or patches. A suitable adhesive is Century Adhesive A-305-IV manufactured by Century Adhesives Corp. of Columbus Ohio. A strip of silicone coated release paper 57 can cover the adhesive to prevent soiling of the adhesive prior to use. In one embodiment two parallel strips of pressure adhesive can be applied to the garment facing surface 52, each strip of adhesive underlying one of the side core segments 64, 66.

The absorbent core 60 receives and contains body exudates, particularly menses. Suitable materials from which the core segments 62, 64 and 66 include a wide variety of liquid-absorbent materials such as comminuted cellulosic wood pulp fibers, which is generally referred to as airfelt. Examples of other suitable materials include but are not limited to creped cellulose wadding; meltblown polymers, chemically stiffened, modified, or cross-linked cellulosic fibers; absorbent foams; layers of tissue paper; and absorbent gelling materials.

In the embodiment shown in FIGS. 1-7 each of the absorbent core segments 62, 64, and 66 comprises an airlaid airfelt pad of cellulose fibers, which fibers are available from the Foley, Fla. plant of the Buckeye Cellulose Company of Memphis, Tenn. The core segments 62, 64 and 66 can be formed exclusively of cellulose fibers, or alternatively, can include other materials such as absorbent gelling materials in addition to cellulose fibers.

Each of the core segments 62, 64, and 66 can have a length of about 200 millimeters. The widths W1, W2, and W3 (FIG. 3) can each be about 25 millimeters. Each of the core segments 62, 64, and 66 can have a thickness t (FIG. 4) of about 4.9 millimeters in the absence of confining pressure. The combined weight of the core segments 62, 64, and 66 can be about 4.1 grams, with each core segment weighing about 1.37 grams.

The core segments can be airlaid separately, or formed as a unitary pad, and then separated into individual core segments. The following U.S. Patents are incorporated herein by reference for the purpose of disclosing suitable methods for forming airlaid webs of fibers: U.S. Pat No. 4,388,056 issued Jun. 14, 1983 to Lee et al., U.S. Pat. No. 4,551,191 issued November 1985 to Kock et al.; U.S. Pat. No. 4,592,708 issued Jun. 3, 1986 to Feist et al.; and U.S. Pat. Nos. 4,765,780 and 4,908,175 issued Aug. 23, 1988 and Mar. 13, 1990 respectively to Angstadt et al.

Figure 12:
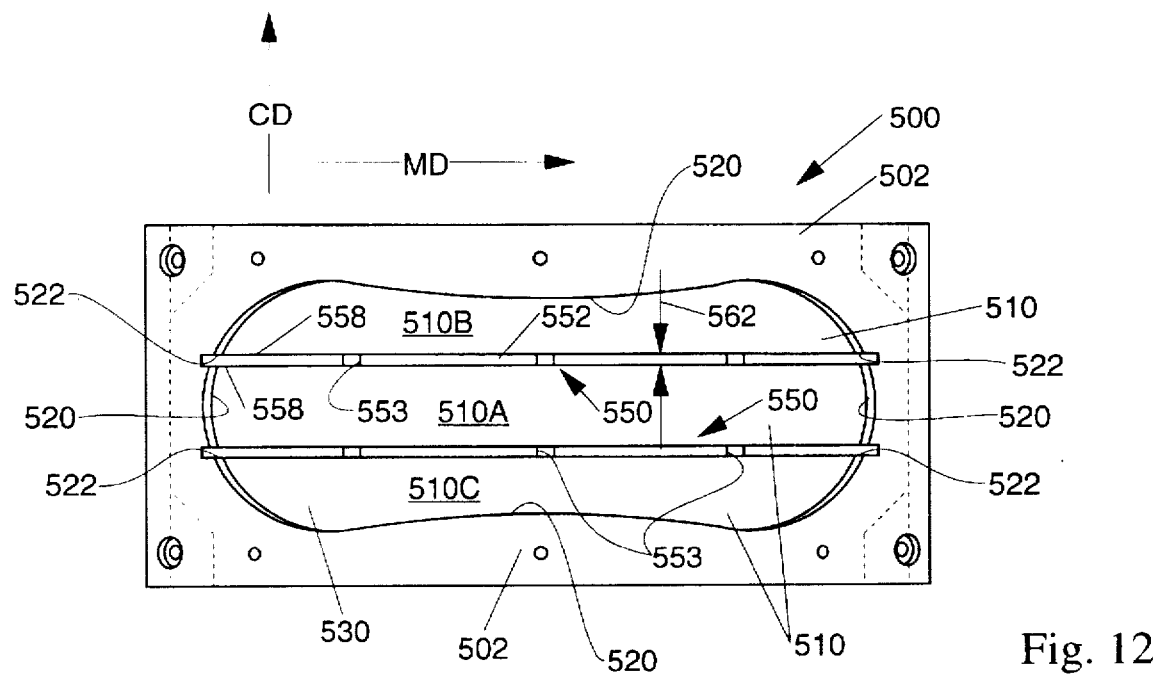
FIG. 12 is a top view of an airfelt deposition mold having a pair of parallel partitions extending in the machine direction and dividing the mold cavity into three mold cavity segments, the mold suitable for forming central and side core segments on an airfelt laydown drum.

Absorbent cores can be formed in discrete cavities on a laydown drum, as disclosed in U.S. Pat. No. 4,859,388 issued Aug. 22, 1989 to Peterson et al., which patent is incorporated herein by reference. FIG. 12 shows an airfelt deposition mold 500 suitable for forming the core segments 62, 64, and 66 on an airfelt laydown drum. A plurality of the molds 500 are mounted on the circumference of the laydown drum, which rotates in a machine direction (MD) indicated in FIG. 12. Each mold 500 has a top arcuate surface 502. Together, the arcuate top surfaces 502 of the molds 500 form the perimeter of the laydown drum. The machine direction corresponds to the longitudinal direction on the sanitary napkin 20. The cross machine direction (CD) is generally parallel to the axis of rotation of the laydown drum and corresponds to the lateral direction on the sanitary napkin 20. The mold 500 comprises a deposition cavity 510 formed in the arcuate top surface 502. The deposition cavity 510 is bounded by a perimeter sidewall 520 and a foraminous bottom wall 530. The foraminous bottom wall 530 can comprise a screen. Airflow through the foraminous bottom wall 530 is created by a vacuum within the laydown drum. The airflow through the foraminous bottom wall 530 carries cellulosic fibers into the cavity 510 for deposition on the foraminous bottom wall 530.

Figure 13:
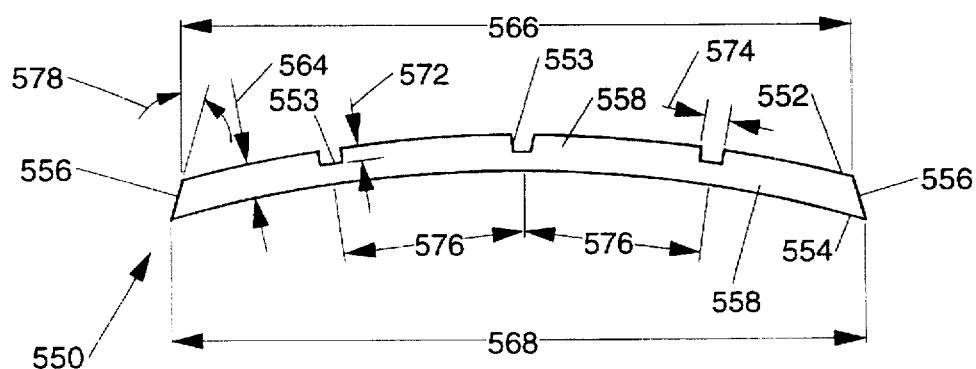
FIG. 13 is a side view of one of the partitions of FIG. 12.

According to the present invention, the cores segments 62, 64, and 66 can be formed to be interconnected in a mold 500 having two generally parallel partitions 550. Referring to FIG. 13, each partition 550 has an arcuate top edge 552 concentric with an arcuate bottom edge 554, and a pair of beveled side edges 556. The edges 552, 554, and 556 extend between oppositely facing sidewalls 558. The beveled side edges 556 engage grooves 522 in the perimeter sidewall 520 of the deposition cavity 510. The foraminous bottom wall 530 supports the bottom edge 554 of each partition 550, and prevents the partition 550 from falling out of the grooves 522. The top arcuate edge 552 of each partition 550 is flush with the top arcuate surface 502 of the mold 500 when the partition 550 is supported in the grooves 522.

The partitions 550 extend in the machine direction and divide the deposition cavity 510 into three cavity segments 510A, 510B, and 510C. Fibers deposited in the cavity segments 510A, B, and C form the core segments 62, 64, and 66, respectively. Each partition 550 can have one or more passageways along its length for interconnecting adjacent cavity segments 510A/B and S510A/C. Referring to FIGS. 12 and 13, the passageways can comprise slots 553 in the top edge 552 which extend in the cross-machine direction through the thickness of the partition 550. Fibers deposited in the slots 553 as the cavity segments 510A–C are filled form a bridge between adjacent cores segments 62/64, and 62/66. The slots 553 thereby provide structural interconnection between the core segments 62/64 and 62/66 as fibers are deposited in the cavity segments. In alternative embodiments the partitions 550 can extend in the cross-machine direction, or in both the machine and cross-machine directions.

For the core segments 62, 64, and 66 described above, the partitions 550 can be formed from stainless steel sheet stock having a thickness 562 of about 1.6 millimeter, and have a height 564 of about 9.5 millimeter. The arcuate top edge 552 can be formed on a radius of about 409 millimeters and have a cord length 566 of about 203 millimeter.

The arcuate bottom edge 554 can be formed on a radius of about 399 millimeters and have a cord length 568 of about 205 millimeters. The slots 553 can have a height 572 of about 3.2 millimeters and a width 574 of about 6.3 millimeters. The slots 553 can be spaced apart on the top edge 552 by an angle 576 of about 8 degrees. The side edges 556 can be beveled at an angle 578 of about 5 degrees.

The mold 500 having partitions 550 provides the advantage that the core segments 62, 64, 66 can be formed and conveyed as a unit, and subsequently separated at any desired point prior to, or after, joining the core segments 62, 64, 66 to other components of the sanitary napkin 20. The mold 500 having partitions 550 can also be used to form core segments 62, 64, and 66 from different materials, or having different density or basis weight characteristics. Different core segments can be formed by directing different materials or different quantities of the same material into the cavity segments 510A–C, or by varying the vacuum within the laydown drum to vary the air drawn through the portion of the foraminous bottom surface 530 subjacent each of the cavity segments 510A–C. Alternatively, the absorbent core 60 can be formed as a single airfelt pad, and then cut longitudinally to provide the individual core segments 62, 64, and 66. However, such cutting can result in undesirable densification of the cut edges of the core segments.

Referring to FIGS. 1–4, the lifting member 100 displaces the central core segment 62 relative to the backsheet 50 and the side core segments 64 and 66. In one embodiment the lifting member 100 comprises a plurality of pleats 115. The pleats 115 provide Z-direction elastic displacement of the central core segment 62 and a portion of the topsheet 40 along the longitudinal centerline 29 relative to the side core segments 64,66 and the backsheet 50. The lifting member 100 thereby provides a bi-level core 60 and a bi-level body facing surface 42 of the topsheet. The pleats 115 also preferably convexly shape a portion of the body facing surface 42 of the topsheet 40 along the longitudinal centerline 29, as shown in FIG. 3. The lifting member 100 thereby maintains contact of the portion of the topsheet 40 along the longitudinal centerline 29 with the wearer's body, and shapes the topsheet 40 to conform to the wearer's body, particularly in the labia, perineum, and/or gluteal groove areas.

The lifting member 100 can comprise a longitudinally extending first pleated element 110 having a plurality of pleats 115 along its length. Each pleat 115 has a Z-direction height H1 (FIG. 4) when the sanitary napkin 20 is in the extended position shown in FIGS. 3 and 4. The lifting member 100 preferably also includes a longitudinally extending second element 120 disposed intermediate the first element 110 and the central core segment 62. The lifting member 100 can also include a longitudinally extending third element 130 disposed intermediate the first element 110 and the backsheet 50. In the embodiment shown in FIGS. 2–4, the second element 120 is positioned between the first element 110 and the first wicking member 70, and the third element 130 is positioned between the first element 110 and the support member 80.

The second and third elements 120 and 130 can be joined to the first element 110 at spaced apart locations along their respective lengths. The pleats 115 extend between the second and third elements 120, 130. The second and third elements 120 and 130 bridge adjacent pleats 115 and stabilize the pleats 115 to help prevent lateral collapse (such as by buckling) of the pleats 115 when the sanitary napkin is in the extended position shown in FIG. 3.

The second element 120 preferably comprises an elastic element. Elastic contraction of the elastic second element 120 gathers the first element 110 about fold lines generally parallel to the lateral centerline 31 to form the pleats 115 along the length of the first element 110. The second element 120 is also preferably elastic to provide a force for maintaining the Z-direction height of the pleats 115, and for restoring the Z-direction height of the pleats 115 when the pleats 115 are compressed by a Z-direction load such as the compressive load 200 shown in FIG. 2. The pleats 115 are compressed by the load 200, such as when the wearer is sitting, to provide for the comfort of the wearer. When the compressive load 200 is removed (e.g., when the wearer stands up), contraction of the elastic second element 120 restores the Z-direction height of the pleats 115 and thereby maintains contact of the topsheet 40 with the wearer's body.

The third element 130 can also comprise an elastic third element 130. In one embodiment both of the second and third elements 120 and 130 are elastic elements, and elastic contraction of one or both of the elastic second and third elements 120, 130 gathers the first elastic element 110 to form the pleats 115. In yet another embodiment the first element 110 can also comprise an elastic element.

The term "elastic element" refers to a component which has a free length, and which can be strained by a tensile force to have a percentage of elongation of at least 35 percent (elongated length greater than or equal to 1.35×free length), and wherein upon release of the tensile force the component contracts to within 5 percent of its free length within ten seconds.

In one embodiment, the ability of the lifting member 100 to restore the Z-direction caliper of the sanitary napkin 20 is relatively unaffected by wetting of the lifting member 100. The lifting member 100 can have a wet caliper reduction which is no more than about 20 percent greater than its dry caliper reduction, and a wet caliper reduction of no more than about eight percent. The wet caliper reduction and dry caliper reduction for the lifting member 100 are measured using the following procedure repeated for four lifting member samples.

The lifting member 100 is adhesively attached to a sheet of polyethylene film having a thickness of about 1.0 mil. The lifting member 100 and polyethylene film are supported on the horizontal surface of an analytical balance, or other suitable scale. The Z-direction caliper of the lifting member 100 above the polyethylene film is measured using a suitable displacement measuring system. A suitable displacement measuring system is an ONO-SOKKI DG 3610 Digital Gauge and an ONO-SOKKI GS-503 Linear Gauge Sensor available from the ONO-SOKKI Corporation of Japan. The Z-direction caliper of the lifting member 100 is measured at various Z-direction load levels applied to the lifting member 100 through a circular load application foot having a diameter of 0.95 inch. The load application foot is connected to the linear gauge sensor.

The lifting member 100 and polyethylene film are placed on the balance, and the balance is tared out to have a zero reading. The initial dry Z-direction caliper of the lifting member 100 is measured with the load application foot just touching the lifting member 100, so that the balance indicates a reading of about zero. The Z-direction load on the lifting member 100 is increased to 32.1 grams in about 5 equal increments, so that the balance indicates a weight of 32.1 grams. The load is then removed, and the unloaded dry Z-direction caliper of the lifting member 100 is recorded with the load application foot just touching the lifting member 100, so that the balance indicates a reading of about zero. For each sample, the difference between the initial dry Z-direction caliper and the unloaded dry Z-direction caliper is divided by the initial dry Z-direction caliper to obtain the percentage change in dry caliper of the sample. The dry caliper reduction is the average of the percentage change in dry caliper for the four lifting member samples.

Each lifting member (and its associated polyethylene sheet) is completely submerged in distilled water for 10 seconds, and then allowed to drain vertically for 10 seconds. The lifting member 100 and polyethylene sheet are then supported on the horizontal surface of the analytical balance, and the balanced tared out to indicate a reading of zero. The initial wet Z-direction caliper of the lifting member 100 is measured with the load application foot just touching the lifting member 100, so that the balance indicates a reading of about zero. The Z-direction load on the lifting member 100 is then increased to 32.1 grams in about 5 equal increments. The load is then removed and the unloaded wet Z-direction caliper of the lifting member 100 is recorded with the load application foot just touching the lifting member 100, so that the balance indicates a reading of about zero. For each sample, the difference between the initial wet Z-direction caliper and the unloaded wet Z-direction caliper is divided by the initial wet Z-direction caliper to obtain the percentage change in the wet caliper of the sample. The wet caliper reduction of the lifting member 100 is the average of the percentage change in wet caliper for the four lifting member samples.

In one embodiment, the lifting member 100 is nonabsorbent. By "nonabsorbent" it is meant that the lifting member 100 has an absorbency capacity of less than 100 percent. The absorbency capacity is the ratio of the weight of the water absorbed by a dry sample to the dry sample weight. A nonabsorbent lifting member 100 is believed to have the advantage that its stiffness and/or its ability to displace the central core segment 62 upward are relatively unaffected by body fluids entering the absorbent article 20, as compared to a lifting member which is absorbent. The absorbency capacity of the lifting member is measured by first weighing the lifting member 100 to obtain its dry weight, and then completely submerging the lifting member 100 in distilled water for 10 seconds.

After 10 seconds the lifting member 100 is removed from the water. The lifting member is then allowed to drain vertically for 10 seconds. Water adhering to the surface of the lifting member is then removed by blotting the lifting member between two pieces of filter paper for 10 seconds. The lifting member 100 is blotted by placing a first piece of filter paper on a dry horizontal surface, placing the lifting member on the first piece of filter paper, placing a second piece of filter paper on top of the lifting member to cover the lifting member, and placing a piece of 0.25 inch thick Plexiglas weighing 0.26 pound on top of the second piece of filter paper to cover the portion of the second piece of filter paper overlying the lifting member. A suitable filter paper for blotting the lifting member 100 is filtration paper having a relatively smooth surface, a particle retention size of greater than about 20–25 micrometers, and a Herzberg filtration speed of about 37 seconds, where the filtration speed is the time for 100 ml of prefiltered water to pass through a 10.0 square centimeter piece of filter paper with a constant head pressure of 10 centimeters of water. A suitable filtration paper is Whatman 4 filtration paper manufactured by Whatman Ltd. of England and available from the Fisher Scientific Company of Pittsburgh, Pa. After blotting the lifting member 100 for 10 seconds, the lifting member 100 is immediately weighed to obtain the wet sample weight. The dry weight is subtracted from the wet weight to yield the grams of water absorbed by the dry sample. The percentage absorbency capacity is obtained by dividing the grams of water absorbed by the dry sample weight, and multiplying the quotient by 100.

In one embodiment the lifting member 100, and particularly the pleats 115, is hydrophobic. A surface is hydrophobic if the contact angle between a liquid and the surface is greater than 90 degrees. The American Chemical Society Publication "Contact Angle, Wettability, and Adhesion,"

edited by Robert F. Gould and copyrighted in 1964 is incorporated herein by reference for the purpose of showing how the contact angle can be determined.

In one embodiment the lifting member 100 extends along the longitudinal centerline 29 of the sanitary napkin 20, and can have a longitudinal length which is approximately equal to the length L of the central core segment 62. The lifting member can have a lateral width C (FIG. 1), corresponding to the width of the second and third members 120 and 130, which is less than the lateral width W1 of the central core segment 60. Without being limited by theory, a relatively large width C provides lateral stability of the lifting member 100, and a relatively small width C enhances fit of the raised portions of the topsheet and core with the labia, perineum, and gluteal groove areas of the body.

The first element 110 can be formed from a number of suitable materials, including but not limited to woven and nonwoven sheet material, plastic films, and natural or synthetic rubber strands. One suitable material from which the first element 110 can be formed is a polypropylene mesh scrim material having a basis weight of about 100 grams per square meter and available as P100 (also designated PC-52) polypropylene mesh scrim from Smith and Nephew Plastics, Ltd. of Gilberdyke, North Humberside, UK. A sheet of such a mesh scrim has about 40 relatively thicker and stiffer primary strands per centimeter (16 strands per inch) running in the sheet machine direction and about 61 relatively thinner and less stiff secondary strands per centimeter (24 strands per inch) running perpendicular to the primary strands in the sheet cross machine direction. The first element 110 can comprise a 6.0 mm wide strip of the P100 (PC-52) mesh cut parallel to the primary strands, so that the primary strands extend along the length of the first element 110, and generally parallel to the longitudinal axis 29 of the sanitary napkin 20. Another suitable material from which the first element 110 can be formed comprises a polypropylene mesh scrim having a basis weight of about 50 grams per square meter (10 lbs/1000 square feet) available as ON7100 polypropylene mesh from the Conwed Company of Minneapolis, Minn.

The elastic second and third elements 120 and 130 can be formed from a number of types of elastic material including natural or synthetic rubber strands, elastic woven or nonwoven materials, and elastic films. One suitable material from which the second and third elements 120 and 130 can be formed is an elastic tape sold by Fulflex, Inc. of Middletown, R.I. as ULTRAFLEX Model 6EX29 elastic tape. The second and third elements 120 and 130 can each comprise a length of such an elastic tape having a width of between about 4.0 and 6.0 mm and a thickness of about 2.0 mm. Alternatively, the elements 120 and 130 can each comprise a 6.0 mm wide strip of EXX-500 elastic sheet material available from the Exxon Chemical Company of Buffalo Grove, Ill. A lifting member 100 having a first element 110 formed of the above PC-52 polypropylene mesh scrim and second and third elements 120, 130 formed of the above ULTRAFLEX tape is nonabsorbent, and has a wet caliper reduction which is less than about 20 percent of its dry caliper reduction, with the wet caliper reduction no more than about 8 percent.

The pleats 115 in the first element 110 can be formed by elastic contraction of one or both of the second and third elements 120,130 relative to the first element 110. For instance, the first element 110 can have a free (unstretched) length which is greater than the free length of the second element 120 and the third element 130. The second and third elements 120 and 130 can be elongated relative to their free lengths and relative to the first element 110. While elongated, the first and second elements 120 and 130 can be attached to the first element 110 at spaced apart locations along the length of the first element 110. When the forces causing the elongation of the elastic elements 120 and 130 are released, the elastic elements 120 and 130 will contract relative to the first element 110, thereby drawing the spaced apart attachment points on the first element 110 together to form the pleats 115.

Percentage elongation is determined by subtracting an elongated length from the free gage length, and dividing the difference by the free gage length. For elastic elements 120 and 130 formed from the ULTRAFLEX elastic tape listed above, a suitable lifting member 100 with pleats 115 can be made by providing a percentage of elongation in the second and third elements 120 and 130 of between about 35 and about 400 percent. The 15 second and/or third elastic elements 120 and 130 can be attached to the first element 110 at locations spaced apart a distance of between about 25.4 mm (1.0 inch) and about 127 mm (5.0 inch) as measured when the elastic elements are elongated and prior to gathering of the first element 110 by contraction of the second and third elements 120 and 130.

The height H1 of the pleats 115 is at least about 10 mm, preferably at least about 15 mm, and more preferably at least about 20 millimeters to provide adequate displacement of the central core segment 62 relative to the side core segments 64 and 66. In the embodiment shown in FIG. 4 the Z-direction height H1 of the pleats 115 is generally uniform along the length L of the lifting member 100. By way of example, the height H1 can be between about 20 mm to about 22 mm. The spacing L1 between adjacent pleats 115 can be between about 15 mm and about 19 mm. For a lifting member 100 having a first element formed from the P100 (PC-52) mesh scrim material listed above and having first and second elastic elements 120, 130 formed from the ULTRAFLEX elastic tape listed above, such a uniform arrangement of pleats 115 can be obtained where the percentage of elongation in the second and third elements 120 and 130 is about 250 to about 300 percent and where the second and third elements 120 and 130 are attached to the first element 110 at locations spaced apart a distance of about 49 mm to about 52 mm as measured when the second and third elements 120 and 130 are elongated and prior to gathering the first element 110 by contraction of the second and third elements 120 and 130. A lifting member 100 having a first element formed from the above listed P100 (PC-52) mesh scrim material and having first and second elastic elements 120, 130 formed from the above listed ULTRAFLEX tape can have a pleat height H1 of 22 mm and a spacing L1 of 16 mm where the percentage of elongation of the second and third elements 120 and 130 is about 300 percent and where the second and third elements are attached to the first element at locations spaced apart a distance of about 50 millimeters as measured when the second and third elements are elongated.

While the height H1 is relatively uniform along the longitudinal axis 29 in FIG. 4, in other embodiments the Z-direction height of the pleats 115 can vary along the longitudinal length L of the lifting member 100. U.S. patent application Ser. No. 08/170,461 filed Dec. 20, 1993, now abandoned, in the name of McFall is incorporated herein by reference for the purpose of disclosing a lifting member 100 having pleats 115 with uniform and varying Z-direction heights.

In another embodiment the lifting member 100 can comprise a wicking member for transporting body fluids in the Z-direction and along the length of the lifting member 100. For instance, the pleated first element 110 can comprise a wicking member and can transport body fluids longitudinally along the length of the lifting member 100, and in the Z-direction from the central core segment 62 and the wicking member 70 to the support member 80. A first pleated element 110 which comprises a wicking member can be formed from apertured or nonapertured plastic films, plastic mesh scrims, or elastic strands treated or formed to be hydrophilic. A suitable first element 110 can be formed from a polypropylene mesh scrim, such as the above PC-52 mesh scrim, treated or formed to be hydrophilic. The mesh scrim can be treated to be hydrophilic by depositing on its surface a layer of hydrophilic meltblown polyethylene fibers, such as are available from the Fibertech Corporation of Landisville, N.J. Alternatively, the mesh scrim can be formed to be hydrophilic by including in the scrim resin additives that bloom to the surface of the scrim and render it hydrophilic. One such additive is a Xantrex polypropylene resin available from the Himont Company of Del. The elastic second and third elements 120 and 130 can be formed from a variety of hydrophilic apertured substrates, including elastomeric films and nonwovens treated or formed to be hydrophilic. A suitable material from which the second and third elements 120 and 130 can be formed is an elastomeric meltblown nonwoven with a basis weight of between about 40 to about 120 grams per square meter coated on both sides with a suitable surfactant to make the surfaces of the nonwoven hydrophilic. A suitable nonwoven is a thermoplastic polyurethane spunbond fabric such as Kanebo Urethane Spunbond available from the Kanebo Company of Osaka, Japan. A suitable surfactant with which the nonwoven can be treated is SILWET surfactant manufactured by the ICI Company of Ostringen, Germany.

Figure 10:
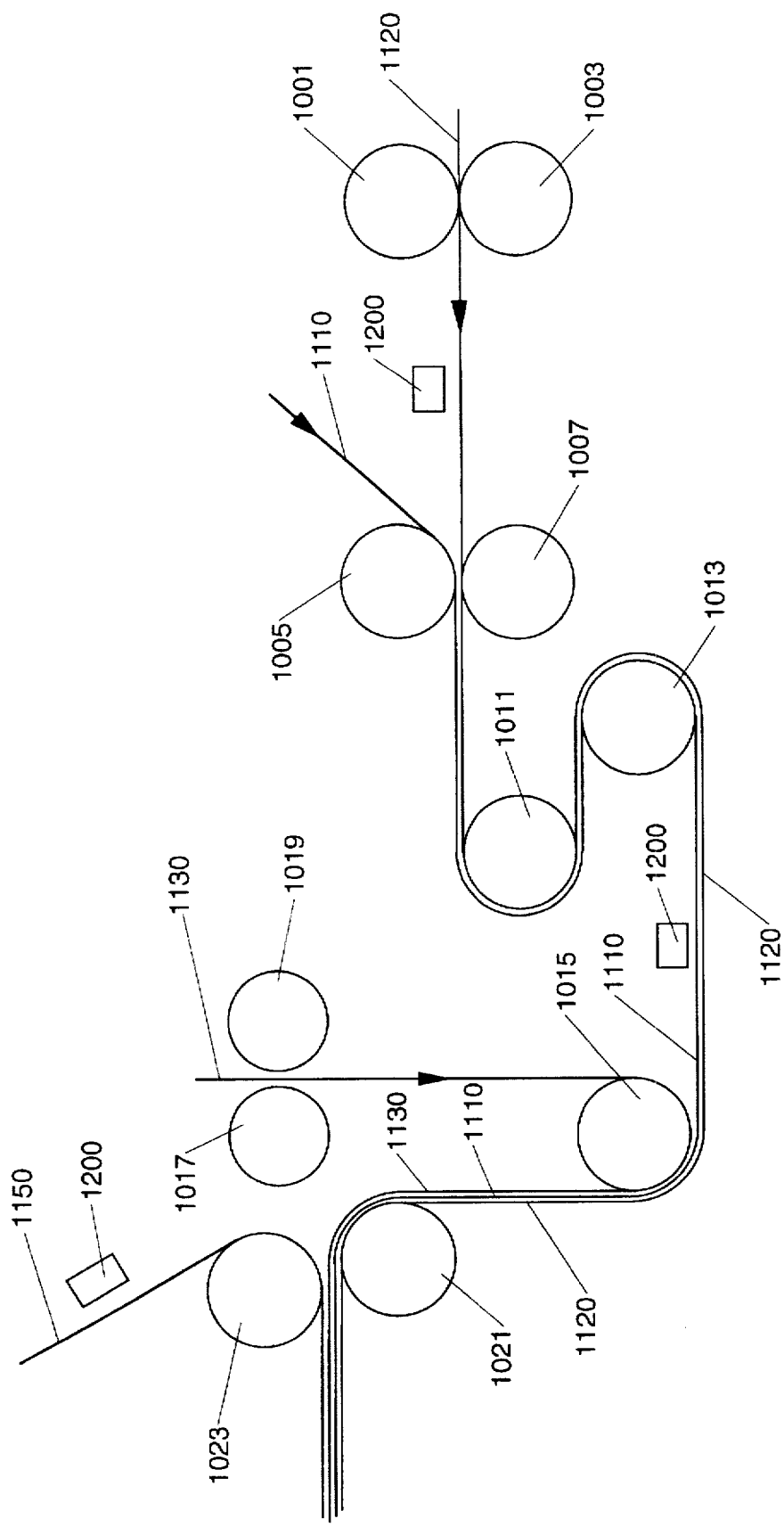
FIG. 10 is a schematic side elevation view of an apparatus for forming the lifting member of the present invention by differentially elongating two or more elements and intermittently joining the differentially elongated elements along their lengths.

FIG. 10 illustrates an apparatus for forming a pleated lifting member 100 and joining the lifting member 100 to another component of the sanitary napkin 20. In FIG. 10, three continuously fed pieces of material are designated as components 1110, 1120, and 1130. By way of example component 1110 can correspond to the first element 110, component 1120 can correspond to the elastic second element 120, and component 1130 can correspond to the elastic third element 130. The components 1120 and 1130 can be bonded to the component 1110 at spaced apart locations along the length of the component 1110, such as with an adhesive. The discussion below refers to adhesive bonding of the components 1100, 1200 and 1300, but it will be understood that other bonding methods can be used. For instance, the components can be thermally or ultrasonically bonded together. Alternatively, the components can be mechanically bonded together in a pressure biased nip between a relief patterned cylinder and an anvil cylinder according to the teachings of above referenced U.S. Pat. No. 4,919,738 issued Apr. 24, 1990 to Ball et al., which patent is incorporated by reference.

The component 1120 is carried at a first web speed through a first nip formed between a first pair of compression rolls 1001, 1003 rotating at a first rotational speed. An adhesive applicator 1200 applies adhesive to a side of the component 1120 at spaced apart locations after the component 1120 exits the nip formed by rolls 1001, 1003. A suitable adhesive is Findley Adhesive H2031 available from the Findley Adhesive Company of Elmgrove, Wis.

The component 1120, along with component 1110, is then directed into a second nip formed by a second pair of compression rolls 1005, 1007. The component 1120 is pressed into engagement with the component 1110 by the second pair of rolls 1005, 1007 to adhesively bond the components 1120 and 1110 together at spaced apart locations. The nip rolls 1005, 1007 can be chilled to prevent buildup of the adhesive.

The surface speed of the rolls 1005, 1007 carries the components 1120 and 1110 through the second nip at a second web speed greater than the first web speed at which the component 1120 is carried through the first nip. This web speed differential stretches the component 1120, and thereby differentially elongates the component 1120 relative to the component 1110 prior to intermittently joining the component 1120 to the component 1110. For example, if the compression rolls have the same diameter, the second pair of compression rolls 1005, 1007 can be rotated at a second rotational speed which is greater than the first rotational speed of the rolls 1001, 1003.

The intermittently joined components 1110 and 1120 exit the second nip and are carried around first and second reversing rolls 1011 and 1013 in a generally serpentine path. An adhesive applicator 1200 then applies adhesive to spaced apart locations on a side of the component 1110 not joined to the component 1120. The web speed around the rolls 1011, and 1013 can be maintained equal to the second web speed to maintain the tensile elongation in the component 1120.

The intermittently joined components 1110 and 1120, along with the component 1130, are then directed around a roll 1015 to press the component 1130 into engagement with side of the component 1110 to which adhesive is intermittently applied. The component 1130 is thereby joined to the component 1110 at spaced apart locations. The web speed around the roll 1015 can be maintained equal to the second web speed to maintain the tensile elongations in the component 1120.

Prior to being joined to the component 1110, the component 1130 can be directed at a third web speed through a third nip formed by a third pair of compression rolls 1017, 1019 rotating at a third rotational speed. The third web speed can be less than the second web speed at which the components 1110, 1120, and 1130 are carried around the roll 1015. This web speed differential stretches the component 1130, so that the component 1130 is differentially elongated relative to the component 1110. If the third web speed is equal to the first web speed, the percent elongation of the component 1130 will be approximately equal to the percent elongation of the component 1120. Alternatively, if the third web speed is less than (or greater than) the first web speed, the percent elongation of the component 1130 will be greater than (or less than) the percent elongation of the component 1120.

The combined components 1110, 1120, and 1130, along with a component 1150, can be directed at a fourth web speed through a fourth nip formed by a fourth pair of compression rolls 1021, 1023. The component 1150 can be a continuous web comprising one or more of the materials from which the backsheet 50 and support member 80 are formed, or alternatively, a continuous web comprising one or more of the materials from which the topsheet 40, wicking member 70, and central core segment 62 are formed. An adhesive applicator 1200 can apply adhesive to a side of the component 1150 prior to engagement of the component 1150 with the component 1130 in the fourth nip. The assembly of components 1110, 1120, 1130, and 1150 can be combined in later operations with other sanitary napkin components to form a completed sanitary napkin 20.

The tension in the stretched components 1120 and/or 1130 can be relaxed, such as by reducing the web speed before or after the components 1110, 1120 and 1130 are combined with the component 1150 in the fourth nip. Once the tension in the stretched components is relaxed, the stretched components will elastically contract relative to the component 1110, and thereby gather the component 1110 to form pleats 115.

A lifting member 100 having pleats 115 with a Z-direction height that varies along the length of the lifting member can be formed by varying one or more of the web speeds with time. The elongation of the component 1120 relative to the component 1110 will then vary along the length of the intermittently joined components. Once the tension in the component 1120 is relaxed, the elastic contraction of the component 1120 relative to the component 1110 will vary along the length of the intermittently joined components, thereby forming pleats 115 having different Z-direction heights. The Z-direction height of the pleats 115 can also be varied along the length of the lifting member 100 by holding the elongation of the component 1120 constant while varying the spacing at which the component 1120, while elongated, is attached to the component 1110. Alternatively, the Z-direction height of the pleats 115 can be varied by varying both the elongation of the component 1120 and the spacing at which the elongated component 1120 is attached to the component 1110.

Figure 11A:
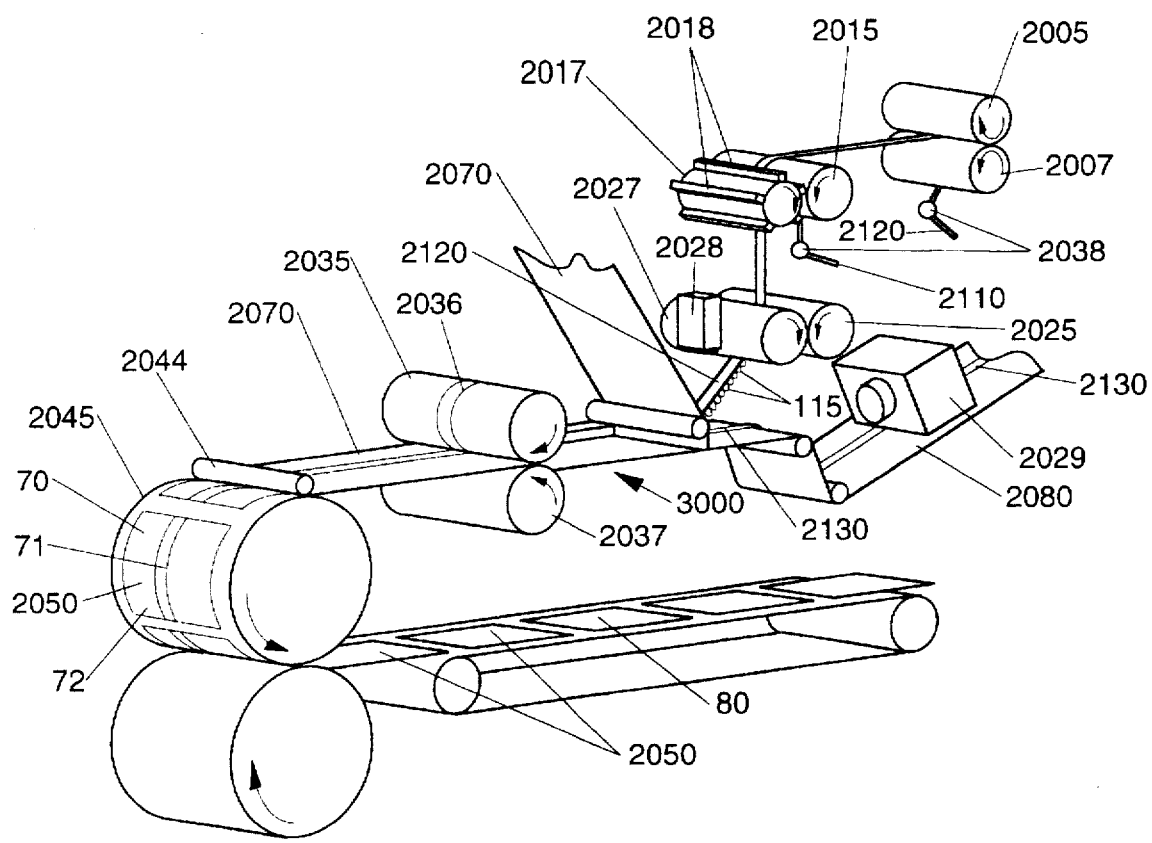
FIG. 11A is a schematic side elevation view of another apparatus for forming the lifting member of the present invention.

FIG. 11A shows an arrangement for forming a pleated lifting member 100 and joining the lifting member 100 to a wicking member 70 and a support member 80. In FIG. 11A, three continuously fed pieces of material are designated as components 2110, 2120, and 2130. By way of example, component 2110 corresponds to the first element 110 of the lifting member 100, component 2120 corresponds to the elastic second element 2120, and component 2130 corresponds to the elastic third element 130. Similarly, continuous webs 2070 and 2080 in FIG. 11A correspond to the wicking member 70 and the support member 80, respectively.

The component 2120 is laterally supported by a guide 2038. Likewise, the component 2110 is laterally supported by a guide 2038. The component 2120 is carried through a nip formed by a pair of stretching rolls 2005 and 2007. The rolls 2005 and 2007 are rotated to have a surface speed less than that of downstream meter rolls 2025 and 2027 to thereby elongate the component 2120. Intermediate the stretch rollers 2005, 2007 and the meter rolls 2025, 2027, the components 2110 and 2120 are carried through a nip formed by a pair of heat sealing rolls 2015 and 2017. The heat sealing rolls 2015, 2017 thermally bond the component 2110 to the elongated component 2120 at spaced apart locations along their lengths. The roll 2017 has a plurality of projections 2018 spaced apart around the circumference of roll 2017 to provide the desired bond spacing along the components 2110 and 2120. For bonding components 2110 and 2120 comprising the above P100 (PC-52) mesh scrim and ULTRAFLEX elastic tape, the surfaces of the rolls 2015 and 2017 can be heated to about 300 degrees Fahrenheit, and the interference between projections 2018 and roll 2015 can be set to zero. The components 2110 and 2120 exit the nip formed by rolls 2015 and 2017 thermally bonded together, with pleats 115 formed in the component 2110.

An adhesive applicator 2028 applies adhesive to the component 2120 after the components 2120 and 2110 exit the nip formed by the meter rolls 2025 and 2027. The adhesive applied by applicator 2028 serves to later bond the component 2120 to the component 2070 at downstream bonding rolls 2035 and 2037. Similarly, an adhesive applicator 2029 applies a coating of adhesive to the components 2130 and 2080. The adhesive applied by the applicator 2029 serves to join the components 2130 and 2080 together as they are conveyed adjacent one another, and also serves to later bond components 2130 and 2080 to the components 2110 and 2070, respectively, at the downstream bonding rolls 2035 and 2037.

Figure 11B:
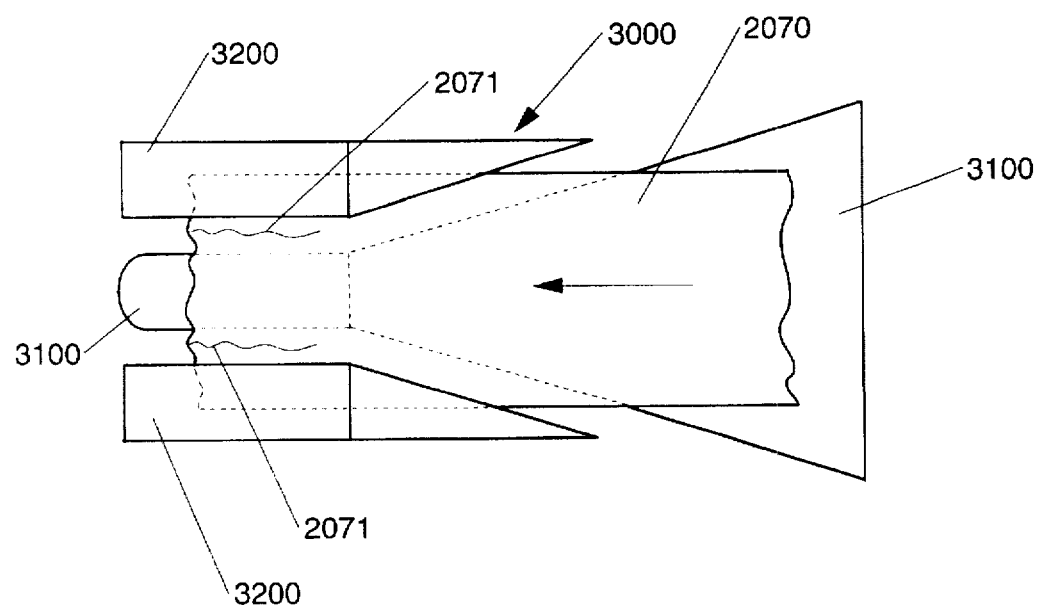
FIG. 11B is a top view of the folding board of FIG. 11A.

Prior to bonding the components at the bonding rolls 2035 and 2037, the component 2070 is directed through a folding board 3000. Referring to FIG. 11B, the folding board 3000 includes a an elevated tongue 3100 and folding plows 3200. As the central portion of the component 2070 is carried over the tongue 3100 and the sides of the component 2070 are carried under the folding plows 3200, parallel folds 2071 are formed in the component 2070 which correspond to the folds 71 in the wicking member 70.

After the component 2070 is folded, the components 2110, 2120, and 2130 are carried through the nip of the bonding rolls 2035 and 2037 between the components 2070 and 2080. The bonding roll 2035 includes a circumferentially extending groove 2036 for accommodating the components 2110, 2120, and 2130 which are sandwiched between the components 2070 and 2080. The continuous laminate of components exiting the bonding rolls 2035 and 2037 is cut to the desired length to form individual tissue/lifting member laminates 2050, each comprising a support member 80, a wicking member 70, and a lifting member 100 disposed between the members 70 and 80. A cut and slip assembly, such is manufactured by the Curt G. Joa Company of Sheboygan Falls, Wis. can used to cut the continuous components to the desired length. Such a cut and slip assembly can include a cutting roll 2044 and a vacuum drum 2045 for carrying the laminates 2050 to a downstream conveyor, at which point the laminates 2050 can be joined to one or more other components of the sanitary napkin 20.

The lifting member 100 shown in FIGS. 1–5 has a longitudinally extending pleated element 110. Such a lifting member has the advantage that it can be relatively easily manufactured by the continuous process described above, and maintains its resiliency even after being compressed for extended periods of time (e.g., when the sanitary napkin is packaged prior to use.) Of course, other lifting members can be used without departing from the scope of the present invention. U.S. patent application Ser. No. 08/170,487, now abandoned, Sanitary Napkin Having Internal Shaping Component filed Dec. 20, 1993 in the name of Bergman and U.S. patent application Ser. No. 07/605,583, now abandoned, Sanitary Napkin Having Components Capable of Separation in Use filed Oct. 29, 1990 in the name of Visscher et al. are incorporated herein by reference for the purpose of showing components capable of providing relative Z-direction displacement of different portions of a sanitary napkin.

The wicking member 70 conveys body exudates from the central core segment 62 to the first and second side core segments 64 and 66. The wicking member 70 can also provide lateral support to the lifting member 100. A preferred wicking member 70 comprises one or more webs of cellulosic fibers, each web having a basis weight of between about 10 grams per square meter and 65 grams per square meter. A particularly preferred wicking member 70 comprises a tissue paper web have a basis weight of about 42 grams per square meter. The wicking member 70 is preferably made according to the teachings of U.S. Pat. No. 4,637,859 issued Jan. 20, 1987 to Trokhan, which patent is incorporated by reference.

The support member 80 transfers loads from the lifting member 100 to the backsheet 50. The support member 80 preferably has a lateral width greater than the lateral width C of the lifting member 100 to distribute loads from the lifting member across a portion of the width of the backsheet 50. The support member 80 can also convey fluids along its length and width. A preferred support member 80 comprises one or more webs of cellulosic fibers having a basis weight of between about 10 grams per square meter and 65 grams per square meter. A particularly preferred support member 80 comprises a tissue paper web have a basis weight of about 42 grams per square meter. The support member 80 is preferably made according to the teachings of above referenced U.S. Pat. No. 4,637,859.

Referring to the exploded view of FIG. 5, the core segments 62, 64, and 66 are joined to the secondary topsheet layer 46 by adhesive attachments 169. The adhesive attachments 169 can comprise Findley H2031 hot melt adhesive. Another suitable adhesive from which attachments 169 can be formed is Findley H4031 adhesive available from the Findley Adhesive Company. The central core segment 62 is joined to the central portion 72 of the wicking member 70 by an adhesive attachment 177, and the side core segments 64 and 66 are joined to the backsheet 50 by adhesive attachments 179. The adhesive attachments 177 and 179 can comprise one of the Findley H2031 or H4031 adhesives listed above.

The second element 120 of the lifting member 100 is joined to the central portion 72 of the wicking member 70 by an adhesive attachment 187. The side portions 74 and 76 of the wicking member 70 are joined to the side portions 84 and 86, respectively, of the support member 80 by adhesive attachments 189. The adhesives attachments 187 and 189 can comprise one of the above Findley adhesives. The third element 130 of the lifting member 100 is joined to the central portion 82 of the support member 80 by an adhesive attachment 191. The support member 80 is joined to the backsheet 50 by adhesive attachments 193. The adhesive attachments 191 and 193 can comprise one of the above Findley adhesives.

The Applicants have found that the present invention improves the ability of a sanitary napkin to receive and hold body fluids. Applicants have found that compared to a sanitary napkin having a single piece airfelt core with no lifting member 100, the sanitary napkin 20 shown in FIGS. 1–5 provides equivalent body fluid holding capacity with a reduced quantity of airfelt. In particular, the Applicants found that the sanitary napkin 20 shown in FIGS. 1–5 having a total of about 4.2 grams of airfelt in the core segments 62, 64, and 68 and about 1.4 grams of tissue paper in the wicking and support members 70 and 80 provides equivalent fluid holding capacity compared to a sanitary napkin having a single piece airfelt core weighing about 9.2 grams.

Figure 6:
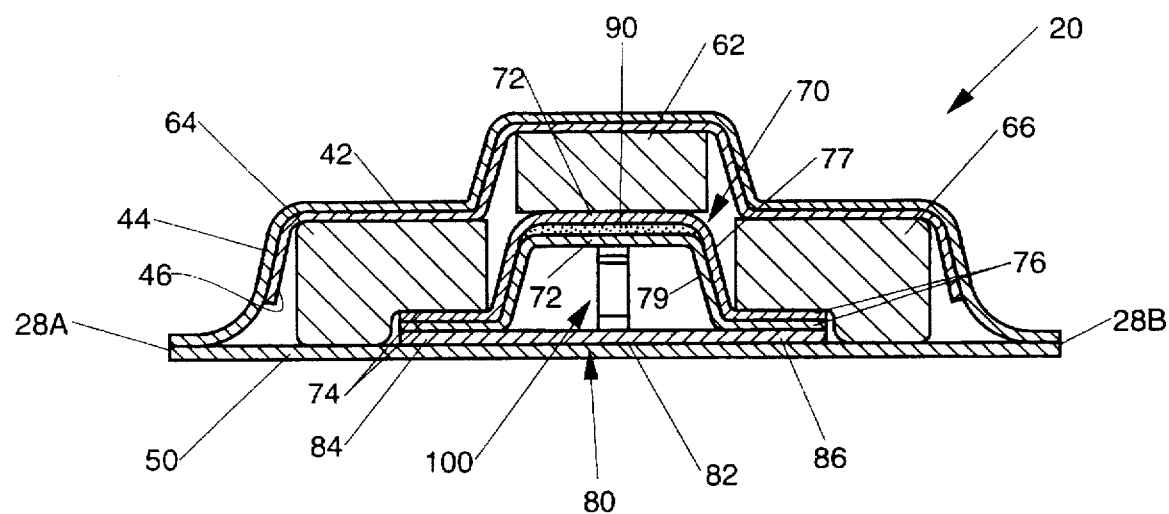
FIG. 6 is a section view similar to that of FIG. 3, showing a laminate of absorbent gelling material sandwiched between two tissue paper webs, the absorbent gelling material and tissue paper webs positioned intermediate a lifting member and a central core segment.
Figure 7:
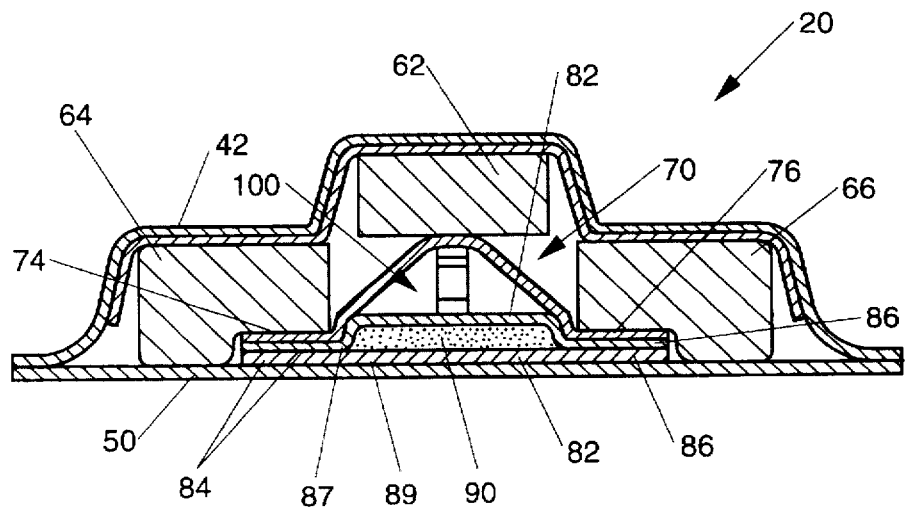
FIG. 7 is a section view similar to that of FIG. 3, showing a laminate of absorbent gelling material sandwiched between two tissue paper webs, the absorbent gelling material and tissue paper webs positioned intermediate a lifting member and the backsheet.

FIGS. 6 and 7 show alternative embodiments of the present invention. In FIG. 6 the wicking member 70 comprises a pair of tissue webs 77 and 79. Each of the tissue webs 77 and 79 has a central portion 72 disposed intermediate the lifting member 100 and the central core segment 62, and first and second side portions 74 and 76. The first side 74 of the tissue web 77 can be joined, such as by adhesive, to the first side portion 74 of the web 79. Similarly, the second side portion 76 of the tissue web 77 can be joined to the second side portion 76 of the web 79. An absorbent gelling material 90 is disposed intermediate the central portions 72 of the tissue webs 77 and 79. The lifting member 100 displaces the absorbent gelling material 90 in the Z-direction relative to the side core segments 64 and 66. The absorbent gelling material 90 can be adhesively joined to one or both of the tissue webs 77 and 79. The absorbent gelling material 90 serves as a storage zone for body liquids passing through the central core segment 62, and increases the liquid holding capacity of the sanitary napkin 20 over that which is available in the core segments 62, 64, and 66 alone. The arrangement shown in FIG. 6 provides the advantage that the absorbent gelling material 90 is positioned adjacent the central core segment 62, and can thereby rapidly acquire body fluids deposited along the longitudinal centerline 29 of the sanitary napkin 20.

An absorbent gelling material is a material which swells upon wetting and absorbs at least about 20 times its weight in water. Such absorbent gelling materials include but are not limited to silica gels and organic compounds such as crosslinked polymers. Particularly preferred absorbent gelling materials are hydrolyzed acrylonitrile grafted starch, acrylic acid grafted starch, polyacrylates and isobutylene maleic anhydride copolymers, or mixtures thereof U.S. Pat. Re 32,649 reissued to Brandt et al. Apr. 19, 1988 is incorporated herein by reference for the purpose of showing suitable absorbent gelling materials.

In FIG. 7 the support member 80 comprises a pair of tissue webs 87 and 89. Each of the tissue webs 87 and 89 has a central portion 82 disposed intermediate the lifting member 100 and the backsheet 50, and first and second side portions 84 and 86. The first side portion 84 of the tissue web 87 can be joined, such as by adhesive, to the first side portion 84 of the web 89. Similarly, the second side portion 86 of the tissue web 87 can be joined to the second side portion 86 of the web 89. An absorbent gelling material 90 is disposed intermediate the central portions 82 of the tissue webs 87 and 89. The absorbent gelling material 90 can be adhesively joined to one or both of the tissue webs 88 and 89. The absorbent gelling material 90 serves as a storage zone for body liquids conveyed by the wicking member 70 from the central core segment 62. The arrangement shown in FIG. 7 provides the advantage that the lifting member 100 does not lift both the central core segment 62 and the absorbent gelling material 90, and the body fluids are contained at a location spaced from the wearer's body by the lifting member 100.

Figure 8:
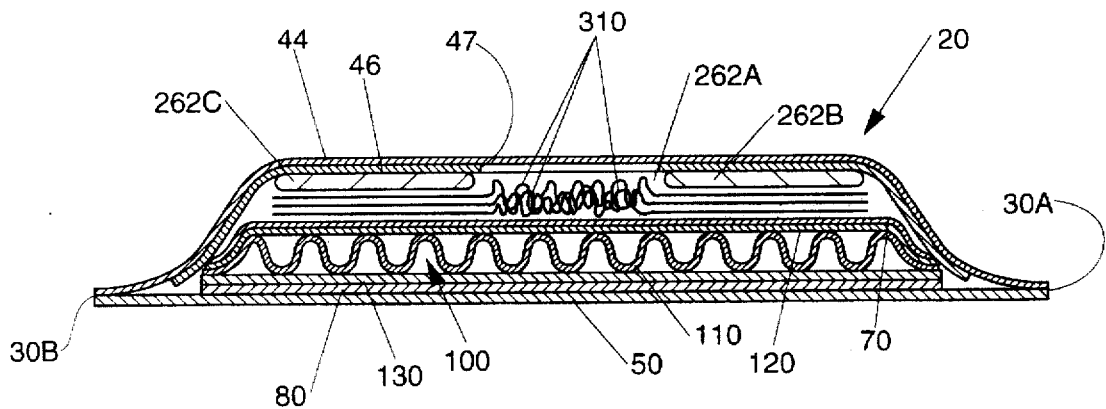
FIG. 8 is a section view similar to that of FIG. 4 showing a central core segment comprising a low density acquisition region having longitudinally extending capillary channel fibers.
Figure 9:
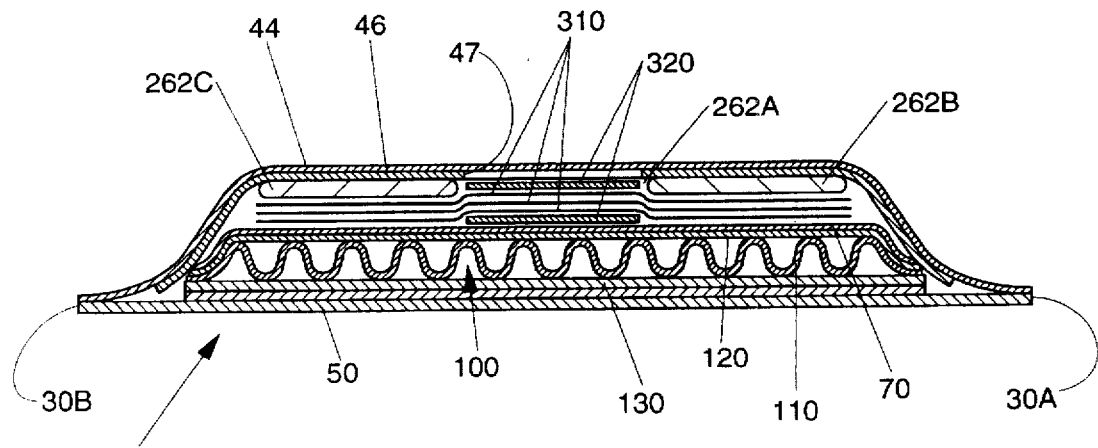
FIG. 9 is a section view similar to that of FIG. 4 showing an alternate embodiment of a central core segment comprising a low density acquisition region having longitudinally extending capillary channel fibers.

FIGS. 8 and 9 disclose alternate embodiments of the present invention wherein the central core segment 62 comprises an acquisition zone 262A having a density less than the density of the airfelt first and second side core segments 64 and 66. The relatively low density acquisition zone 262A is positioned in the area of typical fluid deposition to quickly acquire and distribute liquids within the sanitary napkin 20. U.S. Pat. No. 4,834,735 issued May 30, 1989 to Alemany et al. discloses high density absorbent members having lower density acquisition zones, and is incorporated herein by reference. The relatively low density acquisition zone 262A preferably has a density less than about 0.12 grams per cubic centimeter under a confining pressure of 0.1 pounds per square inch.

Referring to FIG. 8, the acquisition zone 262A is positioned along the longitudinal centerline 29 so that the lifting member 100 displaces the acquisition zone 262A in the Z-direction relative to the side core segments 64 and 66. The acquisition zone 262A is registered with an opening 47 in the secondary topsheet layer 46 so that fluids deposited on the body facing surface 42 of the topsheet 40 along the longitudinal centerline 29 can directly enter the acquisition zone 262A from the primary topsheet layer 44. The acquisition zone 262A can be positioned intermediate relatively higher density forward and rearward airfelt segments 262B and 262C.

In one embodiment acquisition zone 262A is constructed to transport body fluids passing through the opening 47 in a direction generally parallel to the longitudinal centerline 29 of the sanitary napkin 20. A portion of the body fluids carried from the opening 47 toward the ends 30A and 30B by the acquisition zone 262A are then stored in the airfelt segments 262B and 262C, and the remaining body fluids are transported laterally and in the Z-direction by the wicking member 70 for storage in the first and second side core segments 64 and 66.

The acquisition zone 262A can comprise a plurality of longitudinally oriented capillary channel fibers 310 for transporting body fluids in a direction parallel to the longitudinal centerline 29 of the sanitary napkin 20. Portions of the capillary channel fibers 310 registered with the opening 47 are preferably bonded to the primary topsheet layer 44, such as by adhesive bonding, to enhance transfer of body fluids from the topsheet 40 to the acquisition zone 262A. By "longitudinally oriented" it is meant that the fibers 310 extend in a direction generally parallel to the longitudinal centerline 29 of the sanitary napkin 20. The term "capillary channel fiber" refers to a fiber having a cross-section forming an open channel passageway for transporting fluid along the length of the fiber. The fiber cross-section can comprise a number of different shapes, including but not limited to C-shapes, V-shapes, and H-shapes. The following documents are incorporated by reference for the purpose of disclosing such capillary channel fibers: U.S. Pat. No. 5,281,208 issued Jan. 25, 1994 to Thompson et al.; U.S. Pat. No. 5,200,248 issued Apr. 6, 1993 to Thompson et al; PCT Publication WO 93/02235 Fibers Capable of Spontaneously Transporting Fluids published Feb. 4, 1993 in the name of Phillips and having a U.S. Priority date of Jul. 23, 1991; and EP Application 0391814 Fibers Capable of Spontaneously Transporting Fluids published Oct. 10, 1990 in the name of Phillips and having a U.S. Priority date of Apr. 4, 1989.

The acquisition zone 262A can comprise a tow bundle of longitudinally oriented capillary channel fibers 310. The term "tow bundle" refers to a collection of generally parallel fibers having substantially the same fiber length. The tow bundle of capillary channel fibers can have a total denier of between about 25,000 to about 60,000 grams per 9000 meters of tow length, and can have a total weight of about 0.25 gram to about 1.5 gram. The capillary channel fibers 310 in the tow bundle are preferably located in at least the central third of the sanitary napkin 20 as measured along the longitudinal centerline 29, and can extend substantially the full length of the absorbent core 60, as shown in FIG. 8.

In one embodiment, the tow bundle of capillary channel fibers 310 can have a total denier of about 50,000 and a weight of about 1.0 gram. The fibers 310 can comprise helically crimped polyethylene-terephthalate (PET) fibers having a crimping frequency of about 3 crimps per inch, a crimp amplitude of about 0.45 mm, and a relatively deep C shaped cross-section having a channel width of about 55 micron and a channel depth of about 102 micron, with a denier per fiber of about 24 grams per 9000 meters. Such a tow bundle of fibers is manufactured by the Eastman Chemical Company of Kingsport, Tenn. under the designation 4SW "Deep C" CX Low Crimp Helical Tow, SW-405.

In another embodiment, the tow bundle of capillary channel fibers 310 can have a total denier of about 25,000. The fibers 310 can comprise helically crimped PET fibers having a crimping frequency of about 2.5 crimps per inch, a crimp amplitude of about 0.9 mm, and a C-shaped cross-section having a channel width of about 53 microns and a channel depth of about 50 microns, with a denier per fiber of about 10 grams per 9000 meters. Such a tow bundle of fibers is manufactured by the Eastman Chemical Company under the designation 4SW "Spread C" CX, Low Crimp Helical Tow, SW407.

In yet another embodiment, the acquisition zone 262A can comprise a carded sliver of staple fibers having a total denier of about 60,000 grams per 9000 meters of sliver length. The fibers of the carded sliver are longitudinally oriented and can have a 6 inch staple fiber length and a fiber denier of about 27 grams per 9000 meters of fiber length. The fibers can be helically crimped PET fibers with a crimping frequency of about 6 crimps per inch, a crimp amplitude of about 0.5 mm, and an H-shaped cross-section having a channel width of about 43 microns, a channel depth of about 61 microns, and a denier per fiber of about 27 grams per 9000 meters. Such a carded sliver is manufactured by the Eastman Chemical Company under the designation 4SW "H" CX, Carded Staple Sliver, SW404.

In yet another embodiment the acquisition zone 262A can comprise cross-linked cellulosic fibers. U.S. Pat. No. 5,183,707 issued Feb. 2, 1993 to Herron et al. is incorporated by reference for the purpose of disclosing cross-linked cellulosic fibers suitable for use in forming the acquisition zone 262A.

In the embodiment shown in FIG. 9, the acquisition zone 262A comprises a tow bundle of longitudinally oriented capillary channel fibers 310 disposed between bonded fiber layers 320. The tow bundle of capillary channel fibers 310 is joined to the bonded fiber layers 320 by any suitable means, including but not limited to adhesive bonding and ultrasonic bonding. The bonded fiber layers 320 serve to rapidly acquire body fluids, and the tow bundle of longitudinally oriented capillary channel fibers 310 distributes the acquired body fluids in the longitudinal direction.

The tow bundle of capillary channel fibers 310 can have a total denier of about 25,000 and comprise PET fibers having a C-shaped cross-section with a channel width of about 50 microns and a channel depth of about 99 microns, with a denier per fiber of about 22 grams per 9000 meters. Such a tow of fibers is manufactured by the Eastman Chemical Company under the designation 4SW "Deep C" CX, Uncrimped Tow, SW406. The tow bundle of capillary channel fibers 310 can have a total weight of about 0.5 grams.

The bonded fiber layers 320 comprise a bonded network of capillary channel fibers and bicomponent binder fibers. The bonded network can comprise about 90 percent by weight capillary channel fibers and about 10 percent by weight bicomponent binder fibers. The bicomponent binder fibers can be thermoplastic binder fibers such as DANAKLON ES C 1.7 dtex×6 mm crimped bicomponent binder fibers. The capillary channel fibers of the bonded fiber layers 320 can be helically crimped, staple length PET fibers having a C-shaped cross-section and a staple length of about 1.5 inch. The capillary channel fibers can have a crimp frequency of about 7.5 crimps per inch, a crimp amplitude of about 0.4 mm, a channel width of about 52 microns, and a channel depth of about 47 microns. Such fibers are manufactured by the Eastman Chemical Company under the designation SW408. The bonded layers 320, combined, can include about 0.45 grams of the capillary channel fibers and about 0.05 grams of the bicomponent binder fibers. The network of fibers can be formed and thermally bonded as described in U.S. patent application Ser. No. 08/141,156, now abandoned, Catamenial Absorbent Structures Having Thermally Bonded Layers for Improved Handling of Menstrual Fluids, and Their Use in Catamenial Pads Having Improved Fit and Comfort filed Oct. 21, 1993 in the name of Richards et al., which patent application is incorporated herein by reference. The bonded layers 320 can have a density of about 0.02 to about 0.06 gram per cubic under a confining pressure of about 0.1 pounds per square inch, and a basis weight of between about 15 to about 45 grams per square meter.

In another embodiment the bonded layers 320 can have a basis weight of about 30 grams per square meter, a density of about 0.035 gram per cubic centimeter under a confining pressure of about 0.1 pounds per square inch, and a Z-direction thickness of about 0.8 mm under a 0.1 pound per square inch confining pressure. The bonded layers 320 can comprise about ninety percent by weight PET capillary channel fibers and about 10 percent by weight bicomponent binder fibers. The binder fibers can comprise DANAKLON ES C 1.7 dtex 6 mm bicomponent fibers. The capillary channel fibers can have a denier per fiber of 22 grams per 9,000 meters, a crimp frequency of 3.6 crimps per inch, a crimp amplitude of about 0.29 mm, a channel width of about 49 microns, and a channel depth of about 97 microns. Such fibers are manufactured by the Eastman Chemical Company under the designation SW376.

While particular embodiments of the present invention have been illustrated and described, the scope of the present invention is defined by the appended claims.

What is claimed is:

1. A mold for forming an airlaid absorbent core, the mold comprising:

a mold top surface;

a deposition cavity formed in the mold top surface, the deposition cavity bounded by a perimeter sidewall and a foraminous bottom wall; and at least one partition dividing the deposition cavity into cavity segments.

2. The mold recited in claim 1 comprising a pair of generally parallel partitions.

3. The mold recited in claim 2, wherein the mold forms a portion of the perimeter of a laydown drum, and wherein the partitions extend generally parallel to the direction of rotation of the laydown drum.

4. The mold recited in claim 2 wherein each partition comprises a passageway for interconnecting adjacent cavity segments.

5. A method for forming a segmented absorbent core, the method comprising the steps of:

providing a source of vacuum;

providing a mold, the mold comprising:

a mold top surface;

a deposition cavity formed in the mold top surface, the deposition cavity bounded by a perimeter sidewall and a foraminous bottom wall, the foraminous bottom wall in flow communication with the source of vacuum; and at least one partition dividing the deposition cavity into cavity segments, each partition providing an interconnection between adjacent cavity segments;

depositing material into each of the cavity segments to form interconnected core segments; and separating the interconnected core segments subsequent to forming the interconnected core segments.

\* \* \* \* \*